(12) United States Patent
Smith et al.

(10) Patent No.: US 9,400,237 B2
(45) Date of Patent: Jul. 26, 2016

(54) OPTICAL METHOD FOR DETECTING DISPLACEMENTS AND STRAINS AT ULTRA-HIGH TEMPERATURES DURING THERMO-MECHANICAL TESTING

(71) Applicant: The United States of America as represented by the Administrator of the National Aeronautics and Space Administration, Washington, DC (US)

(72) Inventors: Russell W. Smith, Hampton, VA (US); H. Kevin Rivers, Yorktown, VA (US); Joseph G. Sikora, Norfolk, VA (US); Mark C. Roth, Suffolk, VA (US); William M. Johnston, Newport News, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 14/215,781

(22) Filed: Mar. 17, 2014

(65) Prior Publication Data

US 2014/0319355 A1    Oct. 30, 2014

Related U.S. Application Data

(60) Provisional application No. 61/791,017, filed on Mar. 15, 2013.

(51) Int. Cl.
*G01J 5/02* (2006.01)
*G01N 3/06* (2006.01)
*G01N 3/60* (2006.01)

(52) U.S. Cl.
CPC .............. *G01N 3/06* (2013.01); *G01J 5/0255* (2013.01); *G01N 3/60* (2013.01)

(58) Field of Classification Search
CPC ............ G01N 3/06; G01N 3/60; G01J 5/0255
USPC ...................................... 250/341.6
See application file for complete search history.

(56) References Cited

U.S. PATENT DOCUMENTS

| 4,436,419 A | 3/1984 | Stetson et al. |
| 4,591,996 A | 5/1986 | Vachon |

(Continued)

FOREIGN PATENT DOCUMENTS

| DE | 10113216 | 10/2002 |
| JP | 01195302 | 8/1989 |

(Continued)

OTHER PUBLICATIONS

VIC-3D, www.correlatedsolutions.com/vic-3d, copyright © 2013 Correlated Solutions, Inc.

*Primary Examiner* — David Porta
*Assistant Examiner* — Edwin Gunberg
(74) *Attorney, Agent, or Firm* — Robin W. Edwards

(57) ABSTRACT

An ultra-high temperature optical method incorporates speckle optics for sensing displacement and strain measurements well above conventional measurement techniques. High temperature pattern materials are used which can endure experimental high temperature environments while simultaneously having a minimum optical aberration. A purge medium is used to reduce or eliminate optical distortions and to reduce, and/or eliminate oxidation of the target specimen.

13 Claims, 7 Drawing Sheets

(56) References Cited

U.S. PATENT DOCUMENTS

| | | |
|---|---|---|
| 4,934,815 A | 6/1990 | Tai et al. |
| 5,426,498 A | 6/1995 | Brueck et al. |
| 5,671,042 A | 9/1997 | Sciammarella |
| 5,900,936 A | 5/1999 | Shirley et al. |
| 5,920,017 A | 7/1999 | Pechersky |
| 6,043,870 A | 3/2000 | Chen |
| 6,452,180 B1 * | 9/2002 | Nistler et al. ............ 250/341.4 |
| 6,590,194 B2 | 7/2003 | Sardana et al. |
| 6,650,405 B2 | 11/2003 | Lam et al. |
| 7,079,257 B1 | 7/2006 | Kirkpatrick et al. |
| 7,231,243 B2 | 6/2007 | Tearney et al. |

FOREIGN PATENT DOCUMENTS

| | | |
|---|---|---|
| JP | 08043038 | 2/1996 |
| JP | 200039308 | 2/2000 |
| JP | 2005291979 | 10/2005 |

* cited by examiner

| Sample # | Base Coat | Speckle Coat | Method |
|---|---|---|---|
| 1 | Alumia Titania 60/40 | Zirconium Oxide | Flame Spray |
| 2 | Alumia Titania 60/40 | Aluminum Oxide | Flame Spray |
| 3 | None | Aluminum Oxide | Flame Spray |
| 4 | None | Zircar Alumina Cement (Ceramic Cement) | Applied with EFD Dispenser |
| 5 | C-2200 Cement (ceramic cement) | Zircar Alumina Cement (Ceramic Cement) | Applied with EFD Dispenser |
| 6 | C-2200 Cement (ceramic cement) | Zirconium Oxide | Flame Spray |
| 7 | None | 800 Green SiC (Ceramic Cement) | Splatter Spray |
| 8 | None | Zircar Alumina Cement (Ceramic Cement) | Splatter Spray |

Figure 3

OPTICAL METHOD FOR DETECTING DISPLACEMENTS AND STRAINS AT ULTRA-HIGH TEMPERATURES DURING THERMO-MECHANICAL TESTING

CROSS-REFERENCE TO RELATED PATENT APPLICATION

This patent application claims the benefit of and priority to U.S. Provisional Patent Application No. 61/791,017 titled "An Optical Method for Detecting Displacements and Strains at Ultra-High Temperatures During Thermo-Mechanical Testing" filed on Mar. 15, 2013, the contents of which are hereby incorporated by reference in their entirety.

STATEMENT REGARDING FEDERALLY SPONSORED RESEARCH OR DEVELOPMENT

The invention described herein was made in the performance of work under NASA contracts and by employees of the United States Government, and is subject to the provisions of the National Aeronautics and Space Act, Public Law 111-314, §3 (124 Stat. 3330, 51 U.S.C. Chapter 201) and 35 U.S.C. §202, and may be manufactured and used by or for the Government for governmental purposes without the payment of any royalties thereon or therefore. In accordance with 35 U.S.C. §202, the contractor elected not to retain title.

FIELD OF THE INVENTION

This invention relates to a method for detecting displacements and strains at ultra-high temperatures. More specifically, the present invention incorporates speckle optics for sensing displacement and strain measurements well above conventional measurement techniques.

BACKGROUND OF THE INVENTION

A need exists to measure displacements and strains for materials subjected to high temperatures at or above 1500° F. One example is materials used for spacecraft which are experiencing atmospheric re-entry. There are also other high temperature environments in which displacements and strain measurements are needed (examples include, but are not limited to, hypersonic flight vehicles, high temperature engine turbines, and high performance engines). Conventional measurement technologies cannot measure displacements and strains at these temperatures because they cannot physically survive or function. Likewise, current optical measurement methods that measure displacements and strains by observing changes in the patterns applied to the observed surface are currently limited to ambient temperatures, or temperatures far less than 1500° F. Existing techniques cannot be used to make these measurements at high temperatures because current materials used to create these patterns cannot survive at such temperatures. There is a need to create a new test methodology to measure displacement and strain at high temperatures and to verify a material's structural performance at those temperatures.

BRIEF SUMMARY OF THE INVENTION

The present ultra-high temperature measurement technique enables the use of conventional optical methods for sensing of displacements and strains at temperatures well above those where these conventional measurement techniques have previously been applicable. High temperature materials are used which can endure an experimental high temperature environment while simultaneously having a minimum optical aberration, such that emissivity differences in these materials can be used to produce a visible pattern that can be used by conventional optical methods.

A test specimen is placed in an Argon purged cavity having a radiation transparent window and an optically transparent window. The test specimen is coated with a base coat and a speckle coat. An external optical measurement system views the speckled side of the test specimen when the specimen is heated to a desired temperature using a radiative heat source. An optical thermal monitoring system views the coated test specimen to monitor temperature distributions across the specimen's coated surface. Patterns emitted from the test specimen, resulting from emissivity differences due to the patterning/specimen material combination, are detected. Temperature levels associated with radiation emitted by the test specimen are monitored. Force is applied to the test specimen, and linear variable differential transducers (LVDTs) are used to detect and measure displacement and strain of the test specimen.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

FIG. 3 is a table of suitable coatings to be applied to a test specimen surface.

DETAILED DESCRIPTION OF THE INVENTION

An ultra-high temperature measurement technique enables the use of conventional optical methods for sensing of displacements and strains at temperatures well above those where these conventional measurement techniques have previously been applicable. Materials used can endure the high temperature environment and have a minimum optical aberration, such that emissivity differences between these materials and/or the base material can be used to establish a pattern that is discernable with computer vision optical systems. The method is also applicable at temperature ranges below 1500° F. where there is the potential for material degradation due to the induced thermal environment.

Optical methods techniques are used to develop full and near field, strain, and displacement measurements for ultra-high temperature testing. The present ultra-high temperature technique enables the use of conventional optical methods for sensing of displacements and strain at temperatures well above those where conventional measurements techniques have been applicable. Specific high temperature materials are used which can endure the experimental high temperature environment while simultaneously having a minimum optical aberration, such that emissivity differences in these materials can be used to produce a visible pattern that can be used by conventional optical methods. An inert gas may be used to purge the test fixture cavity to reduce or eliminate optical distortions as well as to reduce oxidation effects endured by the test specimen during heating.

Figure 1:
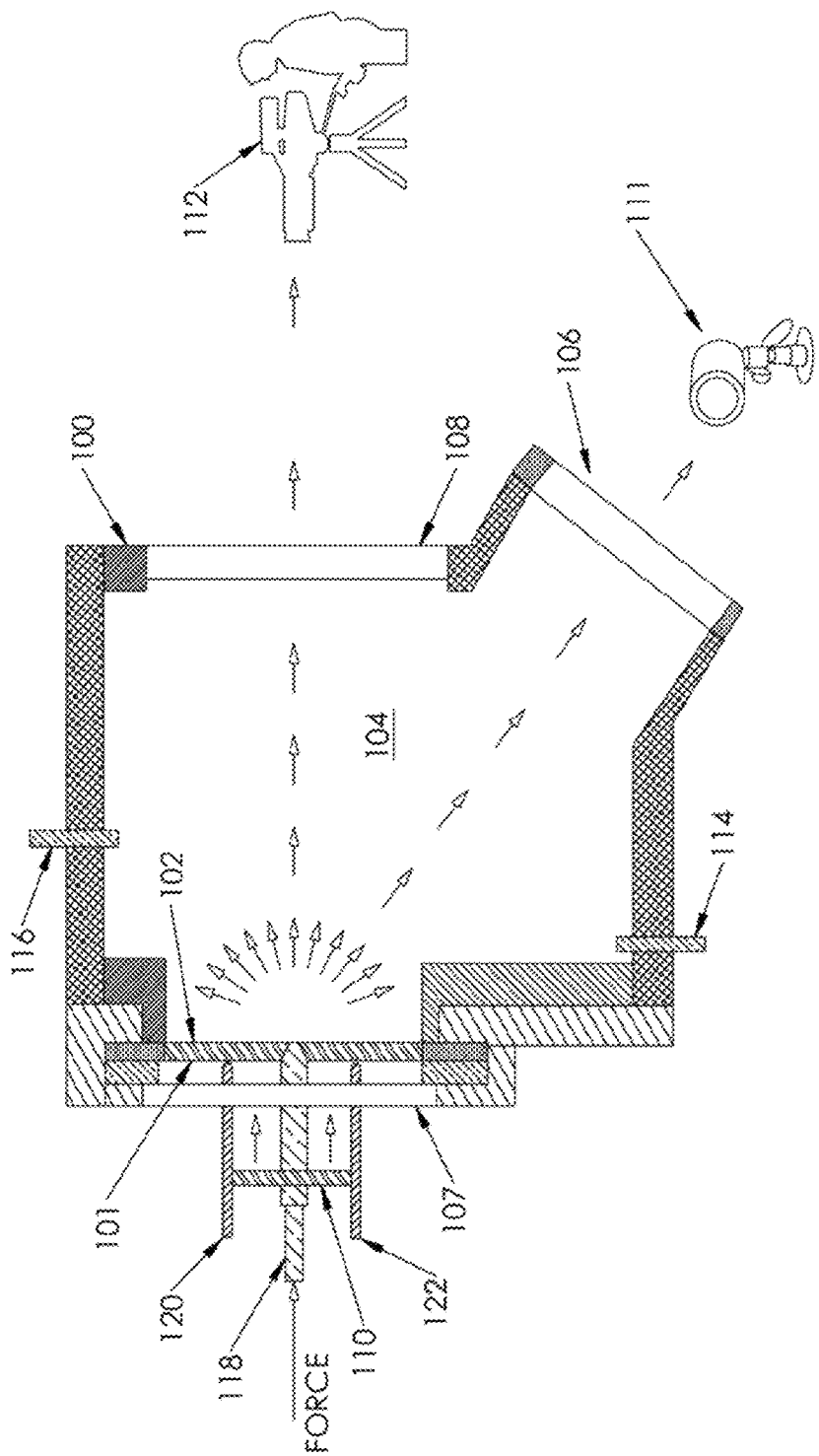
FIG. 1 is a representative test fixture having a test specimen installed in an Argon purged cavity with both a computer vision digital optics system and an Infrared (IR) digital optics system in-situ.

Shown in FIG. 1 is a representation of a test fixture 100 containing a test specimen 101 in an Argon purged cavity 104 that has a radiation transparent window 106 (such as an IR Quartz Window), and an optically transparent window 108 (such as a Digital Image System (DIS) Quartz Window). The test specimen 101 is coated with a base and speckle coat (not shown), A radiative heat source (radiation source) 110 is aligned through window 107 with the back side of the test specimen 101. An external optical measurement system 112, such as a speckled optics computer vision system (image detector) (such as a Hi-Resolution DIS), is aligned to view the speckled side of the test specimen surface 102 through window 108 when it is heated to the desired test temperature using the radiative heat source 110. An additional external optical thermal monitoring system 111, such as an infra-red DIS, is aligned to view the coated test specimen surface 102 through window 106 to monitor temperature distributions across the specimen's coated surface. The computer vision system detects patterns emitted from the test specimen which result from emissivity differences due to the patterning/specimen material combination, whereas the infra-red system monitors temperature levels associated with radiation emitted by the test specimen. The test fixture 100 is purged during a test by an inert gas, such as argon, that is introduced into the cavity 104 through a gas inlet 114 and then evacuated from the cavity 104 through a vent 116. The test fixture 100 has a window 108 through which the speckle pattern on the test specimen surface 102 is viewed during testing by the optical measurement system 112. A rod 118 is aligned in contact with the reverse side of the test specimen 101 to apply force to the test specimen 101 during a test sequence. Also shown are linear variable differential transducers (LVDTs) 120, 122 that are applied to the side of test specimen 101 opposite the cavity 104. The LVDT is an electrical mechanical transducer that converts rectilinear motion of the test specimen's external surface into a corresponding electrical signal and is capable of measuring movements of the object's surface as small as a few ten thousands of an inch up to several inches. The LVDT's 120, 122 are used to detect and measure displacement and strain of the test specimen 101 and validate this new measurement technique.

Figure 2:
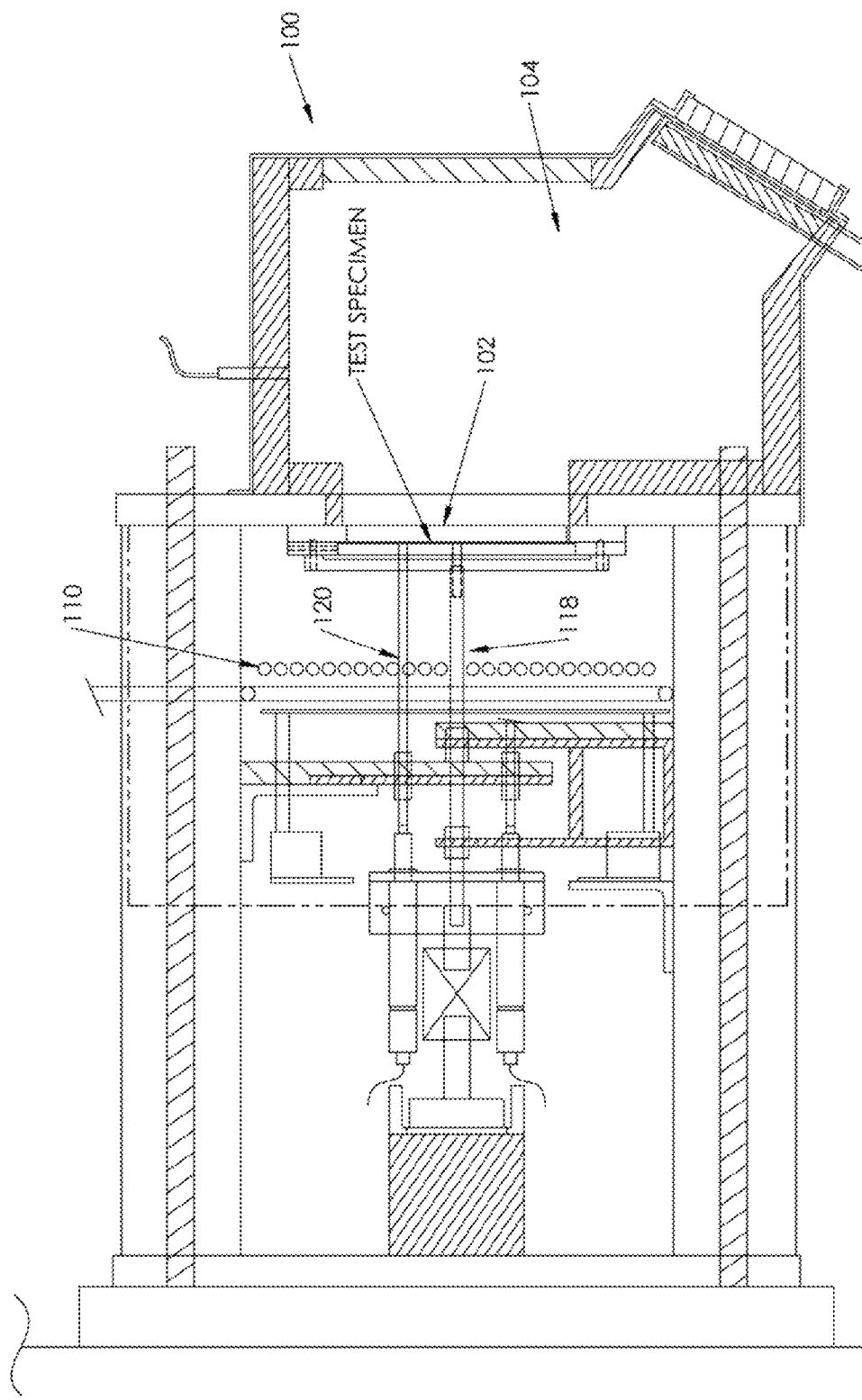
FIG. 2 is a cut away side view of a thermo-mechanical test fixture with a test specimen having a coated surface mounted in an Argon purged cavity with windows for both a computer vision digital optics system and an Infrared (IR) digital optics system in-situ.

FIG. 2 shows a cross sectional side view of a thermal test fixture 100 with a test specimen 101 having a coated surface 102 mounted in a purge-able cavity 104, One LVDT 120 is shown in the test fixture in alignment with test specimen 101. Also shown is rod 118 in contact with test specimen 101 positioned to apply a measured force during testing. A heat lamp 110 is aligned with the test specimen's 101 reverse side (from the speckled surface) 102 facing into the cavity 104 and is used to apply radiative heating.

FIG. 3 lists a sampling of suitable ceramic materials that may be used to create speckled coatings on test specimen 101. These materials are representative of suitable materials for ultra-high temperature environments, but are not exclusive. The materials represented have different emissivities. One may be applied as a base coat to a test specimen surface 102 and the other applied in a speckled pattern onto the base coat. The materials may be applied by flame spray, EFD (electron flame deposition) dispenser or splatter spray or other suitable means. It should be noted that, in some instances, the speckled coating may be applied to a surface without a base coat when the emissivity of the speckled coat allows for differentiation of the emitted radiation. In the alternative, coating of these materials may be applied in patterns that allow the displacement and strains to be measured from emitting surfaces.

Figure 4:
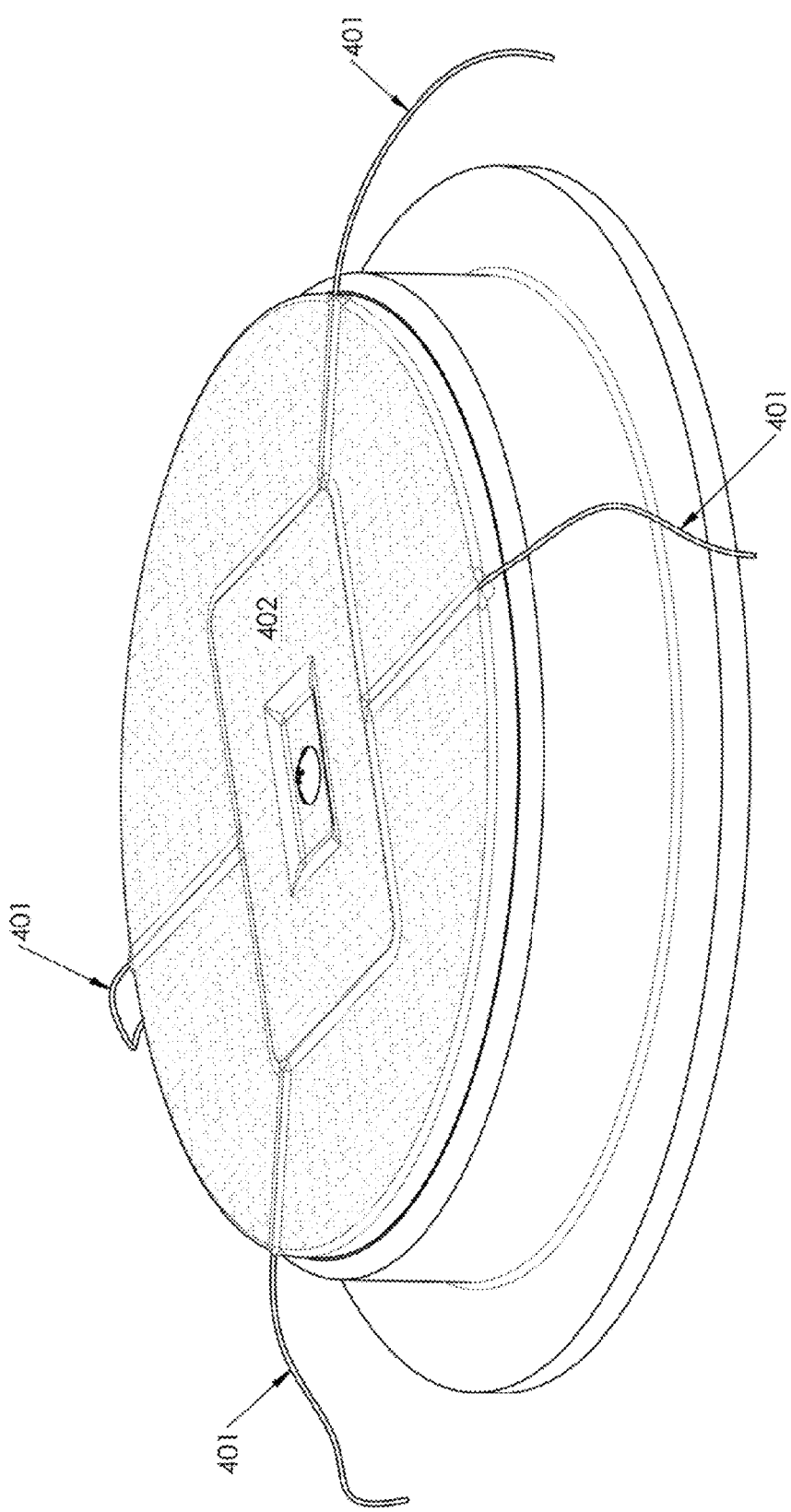
FIG. 4 is a representative test specimen with a speckle coated surface to be measured.

Referring to FIGS. 1 and 4, ceramic material with emissivity value "A" is applied evenly to the surface 102 of a test specimen 101 to provide an optical background. For test specimens of known emissivity, the background coating may not be required. A second ceramic material with emissivity value "B" is sputtered onto the ceramic background material "A" to produce a speckle pattern which allows for the sensing of displacements and strains. The test specimen 101 thus prepared is placed into the cavity 104 which is purged using inert gas, and the test specimen 101 is aligned such that its' surface 102 can be viewed by one or more optical measurement systems 112.

Variances in emissivity of the sensed materials produce optically discernable patterns at ultra-high temperatures. At test temperatures, the speckled pattern on the test specimen surface 102 is viewable due to this variant emissivity between the background and the speckled pattern, allowing the optical system to sense displacement and strain. An alternative test protocol is to coat the surface 102 to be measured with reflective material that can withstand ultra-high temperatures in a pattern that allows emitted radiation patterns to be measured. The emissivity between the coated material and the background material must be sufficiently different to distinguish them from each other.

The present invention is demonstrated in the following described test to determine boss joint failure loads, in a similar installation process as that for the on-orbit repair of space vehicles to include practical simulation of re-entry temperature conditions.

EXAMPLE

Boss Joint

The boss joint test was the third and final test in a sequence of carbon-fiber-reinforced silicon carbide ceramic matrix composite (CMC C/SIC) plate experiments. The flat plate to be tested had a boss plug in its center with an Inner Mold Line MAL) side and Outer Mold Line (OML) side. The IML side was coated with a base coat and a speckled reflecting coat of a different material. Both could withstand ultra-high temperatures but had different emissivities. Referring to FIGS. 1 and 2, the test specimen 101 was placed in the test fixture 100 previously described and a radiative heat source 110 and an optical measurement system 112 were placed in alignment with the test fixture 100 to heat and capture visual images from the test specimen 101. Multiple sensing devices were used. LVDTs 120, 122 were attached to the Inner Mold Line (IML) side of the test specimen 101 to measure displacements. Four opposing pairs of strain gauges were placed on the IML and OML at intervals offset from the center of the boss plug to measure the effects of bending. Three tests were conducted, which consisted of the following:

1. Test 1 was a load control test to the boss joint's ultimate failure load. The ultimate failure load of the first test joint was at a nominal 91 lbs load with a boss joint maximum displacement value of 0.124 in. This test was a straight load to failure.

2. Test 2 was a modified version of Test 1, consisting of an initial tie down load of 60 lbs, then a release to 6 lbs, then a subsequent reload to a nominal ultimate load of 80 lbs. This test was conducted only at ambient thermal conditions.

3. Test 3 was a modified version of Test 2 and consisted of the additional following steps:
   a. An optical shakedown specimen was used to demonstrate that the speckled pattern derived from emissivity differences was detectable at ultra-high temperatures.
   b. Next, an initial shakedown specimen incorporating all required instrumentation, including transducers attached to the test specimen on the OML and IML sides, LVDTs, data recording, temperature gauges, and cavity gas monitoring, were calibrated at ultra-high temperatures.
   c. A final test specimen was placed in the test fixture within an argon purged cavity and heated using a radiant heater array to a target temperature between 2500° F.-3000° F. at the boss plug joint interface with the flat plate section. A pressure was then applied at the boss plug joint in steps to failure. Both the displacement and strain as measured by the transducers and optical measurement system were recorded.

The instrumentation and experimental investigation consisted of the following measurements, in descending levels of criticality, with only the baseline level as a required minimum:

Baseline (minimum):
1. Load values for the induced load into the fastener/boss interface in nominal 5 lb increments.
2. Associated displacements of the boss keyway region, and two radial locations at a distance of 1.5 in from the center of the specimen thru-hole.
3. A sequence of four type "C" thermocouples arranged on the plate's IML section to monitor temperatures in the boss joint area.

Tier 1: Speckled optical displacement values at the various temperatures and loads were measured using a computer vision system.

Tier 2: An IR inspection technique was used during active testing and C-SCAN™ post test was used to ascertain the degree of any induced damage.

The test procedures was as follows:
1. An installation and test procedure consisted of the following.
   i. Initial loading, with associated displacements, was applied to achieve the installation load of 60 lbs.
   ii. Subsequently, the specimen was heated to a steady state condition in the range of 2500° F.-3000° F. with a hold time of 6.7 min. The 60 lb load was maintained throughout the plateau heating. If specimen failure did not occur over the hold period, then the specimen loading was continued, in nominal 2 lb increments, up to final failure while maintaining steady state ultra-high temperatures.
2. An anticipated time frame for steady state conditions was in the 0-15 min range. The test temperature was achieved by a heat array comprised of 15 ft long quartz bulbs, with an output of 6000 Watts each, for a total maximum array output of 90 KW. The heater was operated at a full 480 Volts, 3 phase, to achieve the highest possible specimen temperatures.

The general test outline was as follows.
1. Loading to the initial tie down load of 60 lbs @ 1 Hz to 40 lbs, then 2 Hz to 60 lbs.
2. Thermal loads to achieve steady-state conditions in the 2500° F.-3000° F. temperature range with a record rate of 2 Hz.
3. Upon achieving steady-state temperature, or no more than a 15 min heating time, the data record rate was at 1 Hz.
4. Upon completion of the thermal hold, with a constant 60 lb load, the data record rate was set at 2 Hz and loading to failure commenced.

This test series provided data for boss strength of Space Shuttle plug repair concept for C/SiC cover-plates at ultra-high temperatures. The plug cover-plates tested were approximations of the present boss design used in space vehicles. It is believed that the room temperature tests provide lower bounds on the room temperature boss strength. The third test in the series provided an estimate of the effect of temperature on the boss strength. Therefore, in a comparative context with the two room temperature tests, it provided an estimate of the strength reduction which resulted from temperature increases.

FIG. 4 shows a representative test specimen having a speckle coated surface 402 to be measured. Shown attached to the test specimen are four strain gauges 401. The side shown is the IML side placed inward in the cavity 104 of test fixture 100.

Figure 5:
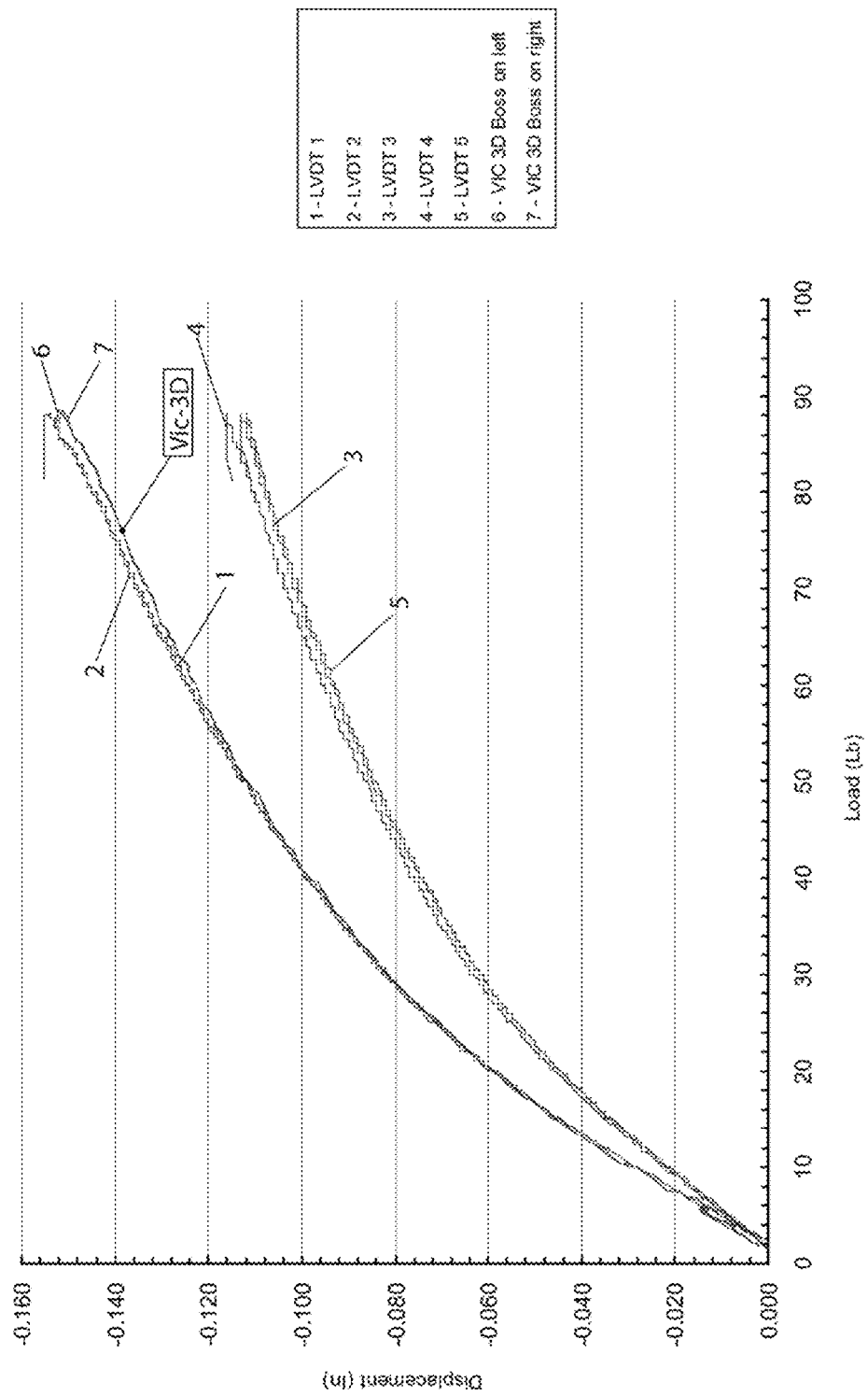
FIG. 5 illustrates measured linear variable differentiation transducer (LVDT) displacement values compared to optical measurement.

FIG. 5 shows a representative graph of LVDT displacement values compared to optical measurements. Four LVDTs, one at the center of the boss plug and LVDTs 2-5 at 1.5 in from the center of the boss plug and 120 degrees apart with LVDT 3 progressing clockwise to LVDT 5 were placed on the OML side of the test specimen surface 102. The accuracy of the LVDTs was (+−) 1 mil. Referring to the graph, both the LVDTs and photo-optical displacement measurements showed good trend agreement, confirming the accuracy of the photo optical speckle coated measurement technique. The nomenclature denoted as "Vic 3D boss on left" and "Vic 3D boss on right" as shown in FIG. 5 was a region in which the boss section had an abrupt cut-away section, and was the most likely area to fail initially during the testing cycle.

Figure 6:
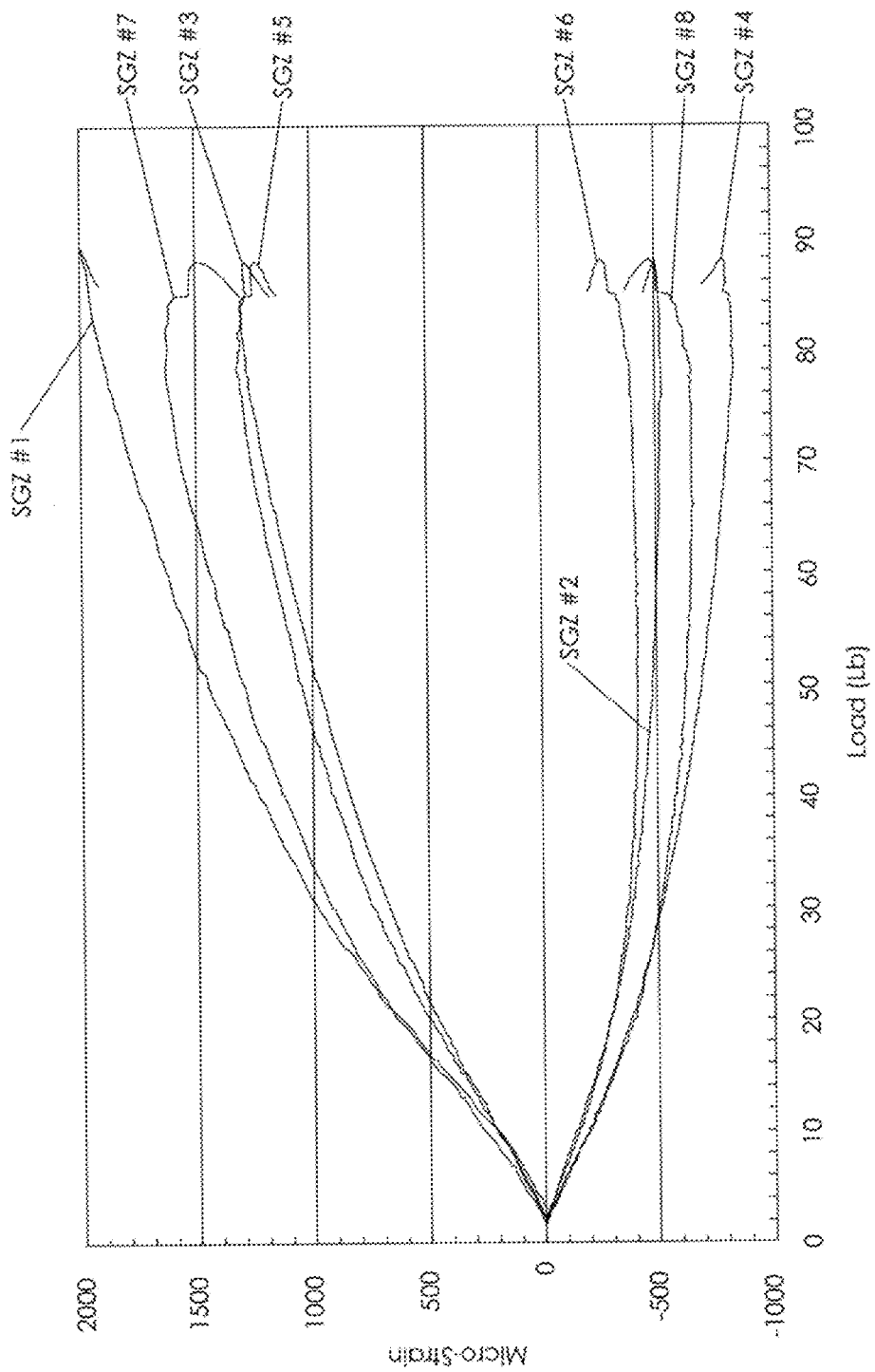
FIG. 6 illustrates measured Inner Mold Line (IML) side and Outer Mold Line (OML) strain gauge responses versus load.

FIG. 6 is a graph of OML and IML strain gage responses vs, load measured by traditional strain gages affixed in opposed pairs to the two surfaces of the test specimen 101. Strain on the vertical (y) axis and load in pounds on the horizontal (x) axis are shown. The measurements above the "0" on the axis are plots of strain measurements taken on the IML side of the test specimen 101, and the measurements below the "0" are measurements on the OML side. There were eight strain gages located in pairs on opposing sides of the test specimen 101. Opposing gage pairs are 1:2, 3:4, 5:6, and 7:8. Gages 1, 3, 5 and 7 are on the IML side and 2, 4, 6, and 8 the OML side. Pairs 1:2 are located at 0.785 in; pairs 3.4, 0.422 in; pairs 5:6, 0.030 in and pairs 7:8, 0.780 in from the center of the boss plug. The gage response shows a high degree of asymmetric bending of the boss plug region.

Figure 7:
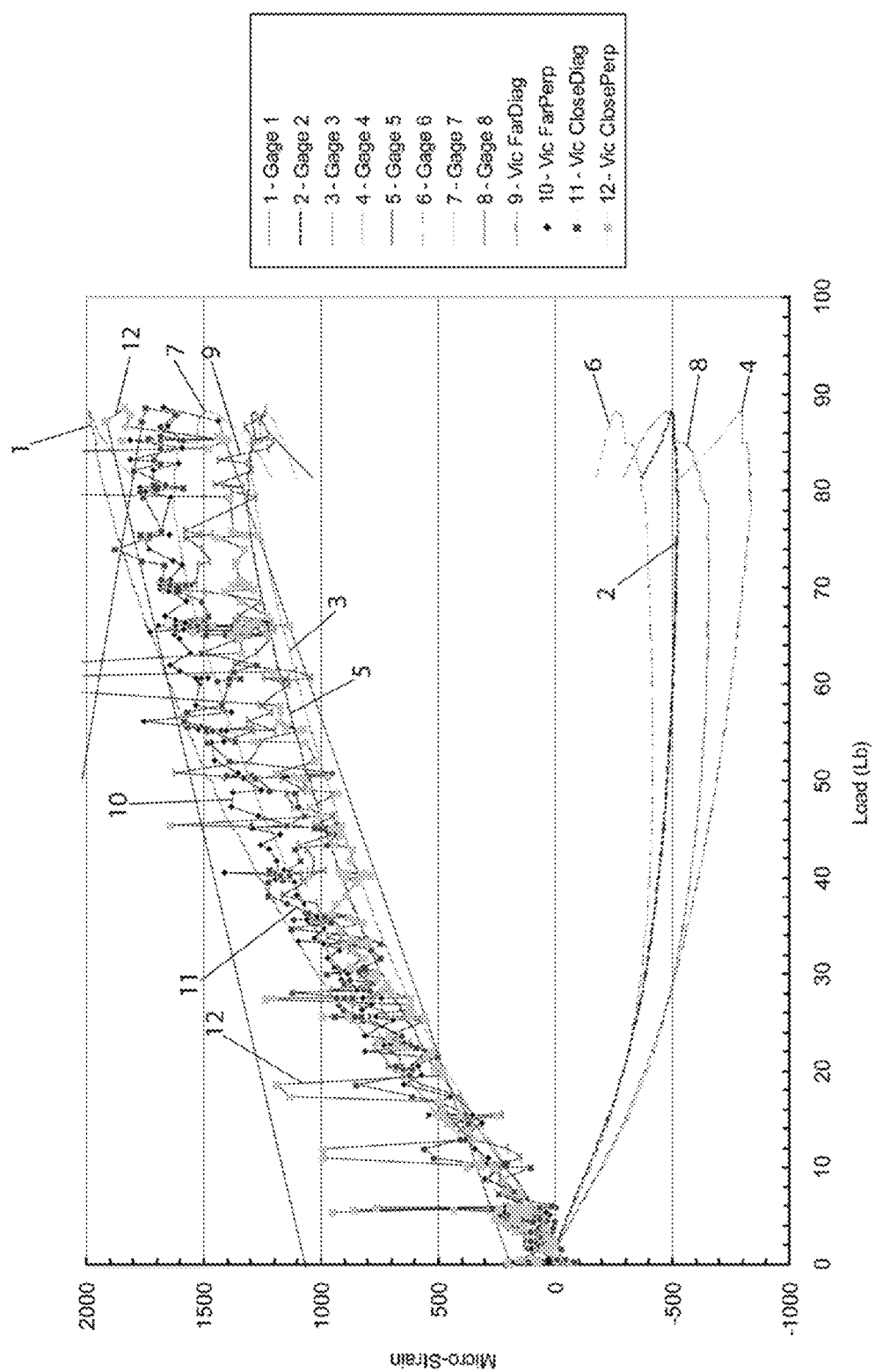
FIG. 7 illustrates strain gage response with optical comparisons.

FIG. 7 is a graph of strain gage response with optical comparisons. The measurement from the same eight strain gages shown in FIG. 6 are super imposed with the measured strain values from the optical measurement of the speckled surface shown as Vic near and far, diagonal and close up locations corresponding to the locations of the strain gages. It is observed that closer observations are more precise, particularly at high strain levels.

In the above described system, thermographic measurement systems which measure energy radiated from a surface in the infrared frequency range could be used in place of the optical measurement system described above. In this instance a pattern may be applied that is discernable in the infrared spectrum and these infrared measurements could be used to calculate strain and deflection.

It is also possible to replace the heating system with a system that selectively excites the surface with energy that can be measured to produce a discernable pattern in any of the detectable frequency ranges (examples include microwave, optical, infrared, ultraviolet frequencies).

It is also possible to correct the discernable optical pattern to improve its quality by employing other computational methods to enhance the images captured prior to processing these measurements using optical measurement systems.

While embodiments and example configurations of the invention have been herein illustrated, shown and described, it is to be appreciated that various changes, rearrangements and modifications may be made therein, without departing from the scope of the invention as defined by the appended claims. It is intended that the specific embodiments and configurations disclosed are illustrative of the preferred and best modes for practicing the invention, and should not be interpreted as limitations on the scope of the invention as defined by the appended claims and it is to be appreciated that various changes, rearrangements and modifications may be made therein, without departing from the scope of the invention as defined by the appended claims.

What is claimed as new and desired to be secured by Letters Patent of the United States is:

1. A method for measuring properties of a specimen, comprising:
   applying a first coating of a first material having a first emissivity to a portion of a surface of the specimen;
   applying a second coating of a second material having a second emissivity to a portion of the surface of the specimen, wherein the first emissivity is different from the second emissivity;
   radiatively heating the surface of the specimen;
   applying mechanical loading to the specimen; and
   observing the difference in emissivity patterns between the first and second materials.

2. The method of claim 1, further comprising:
   coating the surface of the specimen with three or more materials having different emissivities and observing one or more patterns resulting from the emissivity differences in the materials.

3. The method of claim 1, further comprising:
   radiatively heating the surface of the specimen selectively to excite different surface patterns and measuring the patterns resulting from the emissivity differences of the radiated surface.

4. The method of claim 1, further comprising:
   using various infrared radiating materials for the first and second coatings; and observing the emissivity patterns of a material using thermographic techniques.

5. The method of claim 1, further comprising:
   analyzing emissivity patterns with a computer vision system to measure changes in the specimen and calculate displacements and strains.

6. The method of claim 1, further comprising:
   using optical enhancement to improve the emissivity pattern measurements.

7. The method of claim 1, further comprising:
   placing the coated specimen in a sealed cavity;
   purging the cavity with an inert gas;
   heating the specimen in the cavity to a temperature at or above 1500° F.; and
   optically measuring displacements by utilizing the pattern established by the differences in emissivity.

8. The method of claim 1, wherein the second material is reflective and is applied in a speckle pattern.

9. A method for measuring the material properties of a specimen at ultra-high temperatures, comprising:
   coating a portion of the specimen with a reflective material in a speckle pattern that has a different optical emissivity than the specimen to be measured;
   confining the coated specimen in a purgeable cavity;
   purging the cavity with an inert gas;
   heating the specimen in the cavity to temperatures in excess of 1500° F.;
   applying pressure to the specimen in the cavity;
   radiating the specimen;
   collecting radiated patterns from the specimen; and
   measuring differences in the emissivity patterns of the specimen and coated portion.

10. A test fixture for measuring the material properties of a specimen comprising:
    a cavity;
    a mount for the specimen within the cavity;
    a gas inlet and evacuation pump for the cavity;
    a heating source to heat the specimen;
    one or more pressure applicators to apply pressure to the specimen; and
    a window to permit measurement of differential emissivity patterns using an optical measurement system, wherein a coating is applied to the specimen to produce discernable patterns for processing by the optical measurement system.

11. The test fixture of claim 10, further comprising an external optical measurement system arranged to collect optical images of the specimen through the window.

12. The test fixture of claim 10, further comprising one or more transducers affixed to the specimen to measure displacement and strain.

13. The test fixture of claim 10, wherein the cavity is hermetic.

* * * * *